United States Patent [19]

Kobayashi et al.

[11] Patent Number: 5,316,934
[45] Date of Patent: May 31, 1994

[54] EFFECTIVE THROMBOSIS MEDIATED BY HUMAN PROUROKINASE-LIKE POLYPEPTIDES WITH INCREASED BINDING AFFINITY FOR THROMBOSIS

[75] Inventors: Yoh-ichi Kobayashi, Fujisawa; Ken Watabe, Yokohama; Yukuo Mukohara; Masayuki Satoh, both of Odawara; Hiroaki Nakamura, Kawasaki, all of Japan

[73] Assignee: Nippon Soda Co., Ltd., Tokyo, Japan

[21] Appl. No.: 651,363

[22] PCT Filed: Jun. 7, 1990

[86] PCT No.: PCT/JP90/00742

§ 371 Date: Feb. 12, 1991

§ 102(e) Date: Feb. 12, 1991

[87] PCT Pub. No.: WO90/15867

PCT Pub. Date: Dec. 27, 1990

[30] Foreign Application Priority Data

Jun. 13, 1989 [JP] Japan .................. 1-150161
May 15, 1990 [JP] Japan .................. 2-123163

[51] Int. Cl.$^5$ .................. C12N 9/72; C12N 15/58; C12N 15/62; C12N 15/70
[52] U.S. Cl. .................. 435/215; 435/69.6; 435/69.7; 435/252.31; 435/320.1; 536/23.2; 536/23.4; 935/10; 935/14; 935/29; 935/47; 935/73
[58] Field of Search ............. 435/69.1, 172.3, 252.33, 435/320.1, 215, 69.6; 424/94.64; 536/23.2, 23.4; 530/380

[56] References Cited

U.S. PATENT DOCUMENTS 4,892,826 1/1990 Homandberg et al. ............ 435/183

FOREIGN PATENT DOCUMENTS

| 0271227 | 6/1988 | European Pat. Off. ......... 435/127.3 |
| 0273774 | 7/1988 | European Pat. Off. ......... 435/172.3 |
| 0312942 | 4/1989 | European Pat. Off. ......... 435/172.3 |
| 88/03810 | 6/1988 | PCT Int'l Appl. ............... 514/2 |
| 89/00051 | 1/1989 | PCT Int'l Appl. ............... 424/1.1 |

OTHER PUBLICATIONS

Mosher, D. F., et al., 1980, The Journal of Biological Chemistry, 255(3): 1181-1188.
Ichinose A. et al., 1983, FEBS Letters 153(2): 369-371.
Hirosawa, S., et al, 1988, Proceedings of the National Academy of Sciences, USA, 85(18): 6836-40 and 86(5): 1612-1613.
Holmes, W. E., et al., 1987, Journal of Biological Chemistry, 262(4): 1659-1654.
Kornblihtt, A. R., et al., 1985, The EMBO Journal, 4(7): 1755-1759.
Oswald, R. E., et al., 1989, Nature 337:579-582.
Bogusky, M. J., et al., 1989, Biochemistry, 28:6728-6735.
Ichinose A., et al., 1990, The Journal of Biological Chemistry, 265(23): 13411-13414.

*Primary Examiner*—Robert A. Wax
*Assistant Examiner*—William W. Moore
*Attorney, Agent, or Firm*—Joseph C. Mason, Jr.; Ronald E. Smith

[57] ABSTRACT

Human prourokinase-like polypeptides of which oligopeptides having a structure to form a covalent bond with blood clot (thrombus) through enzymatic action of human blood coagulation factor XIII are attached to the NH$_2$-terminal sides of human prourokinase derivatives.

7 Claims, 15 Drawing Sheets

```
         10        20        30        40        50        60
TCTAGATAAGGAGGTGAAAACCATGCAGGCACAACAGATGGTTCAACCTCAGTCACCGGT
                         M  Q  A  Q  Q  M  V  Q  P  Q  S  P  V 70        80        90       100       110       120
TGCTGTTAAGCTCAAGTTTCAGTGTGGCCAAAAGACTCTGAGGCCTCAGTTTAAAATCAT
 A  V  K  L  K  F  Q  C  G  Q  K  T  L  R  P  Q  F  K  I  I 130       140       150       160       170       180
TGGCGGCGAATTCACCACCATCGAGAACCAGCCCTGGTTTGCGGCCATCTACAGGAGGCA
  G  G  E  F  T  T  I  E  N  Q  P  W  F  A  A  I  Y  R  R  H 190       200       210       220       230       240
CCGGGGGGGCTCTGTCACCTACGTGTGTGGAGGCAGCCTCATCAGCCCTTGCTGGGTGAT
  R  G  G  S  V  T  Y  V  C  G  G  S  L  I  S  P  C  W  V  I 250       260       270       280       290       300
CAGCGCCACACACTGCTTCATTGATTACCCAAAGAAGGAGGACTACATCGTCTACCTGGG
 S  A  T  H  C  F  I  D  Y  P  K  K  E  D  Y  I  V  Y  L  G 310       320       330       340       350       360
TCGCTCAAGGCTTAACTCCAACACGCAAGGGGAGATGAAGTTTGAGGTGGAAAACCTAAT
  R  S  R  L  N  S  N  T  Q  G  E  M  K  F  E  V  E  N  L  I 370       380       390       400       410       420
CCTACACAAGGACTACAGCGCTGACACGCTTGCTCACCACAACGACATTGCCTTGCTGAA
 L  H  K  D  Y  S  A  D  T  L  A  H  H  N  D  I  A  L  L  K 430       440       450       460       470       480
GATCCGTTCCAAGGAGGGCAGGTGTGCGCAGCCATCCCGGACTATACAGACCATCTGCCT
  I  R  S  K  E  G  R  C  A  Q  P  S  R  T  I  Q  T  I  C  L 490       500       510       520       530       540
GCCCTCGATGTATAACGATCCCCAGTTTGGCACAAGCTGTGAGATCACTGGCTTTGGAAA
 P  S  M  Y  N  D  P  Q  F  G  T  S  C  E  I  T  G  F  G  K 550       560       570       580       590       600
AGAGAATTCTACCGACTATCTCTATCCGGAGCAGCTGAAAATGACTGTTGTGAAGCTGAT
  E  N  S  T  D  Y  L  Y  P  E  Q  L  K  M  T  V  V  K  L  I
```

*Fig. 5a*

```
        610       620       630       640       650       660
TTCCCACCGGGAGTGTCAGCAGCCCCACTACTACGGCTCTGAAGTCACCACCAAAATGCT
  S   H   R   E   C   Q   Q   P   H   Y   Y   G   S   E   V   T   T   K   M   L 670       680       690       700       710       720
GTGTGCTGCTGACCCACAGTGGAAAACAGATTCCTGCCAGGGAGACTCAGGGGGACCCCT
  C   A   A   D   P   Q   W   K   T   D   S   C   Q   G   D   S   G   G   P   L 730       740       750       760       770       780
CGTCTGTTCCCTCCAAGGCCGCATGACTTTGACTGGAATTGTGAGCTGGGGCCGTGGATG
  V   C   S   L   Q   G   R   M   T   L   T   G   I   V   S   W   G   R   G   C 790       800       810       820       830       840
TGCCCTGAAGGACAAGCCAGGCGTCTACACGAGAGTCTCACACTTCTTACCCTGGATCCG
  A   L   K   D   K   P   G   V   Y   T   R   V   S   H   F   L   P   W   I   R 850       860       870       880       890       900
CAGTCACACCAAGGAAGAGAATGGCCTGGCCCTCTGAGGGTCCCCAGGGAGGAAACGGGC
  S   H   T   K   E   E   N   G   L   A   L   *

910       920       930       940       950       960
ACCACCCGCTTTCTTGCTGGTTGCGATTTTGCAGTAGAGTCATCTCCATCAGCTGTAAGA 970       980       990      1000      1010      1020
AGAGCTGGGAATATAGGCTCTGCACAGATGATTGCCTGTGCCACCGACCAGGGCGAACGA 1030      1040
CAATAGCTTTACCCTCACAAGCTT
```

*Fig. 5b*

```
         10        20        30        40        50        60
TCTAGATAAGGAGGTGAAAACCATGAACCAGGAACAGGTGTCTCCGTTGACTTTGCTTAA
                         M  N  Q  E  Q  V  S  P  L  T  L  L  K 70        80        90       100       110       120
GCTGAGCAACGAGCTCCACCAGGTTCCGTCGAACTGTGACTGTCTAAATGGAGGAACATG
 L  S  N  E  L  H  Q  V  P  S  N  C  D  C  L  N  G  G  T  C 130       140       150       160       170       180
TGTGTCCAACAAGTACTTCTCCAACATTCACTGGTGCAACTGCCCCAAAGAAATTCGGAGG
 V  S  N  K  Y  F  S  N  I  H  W  C  N  C  P  K  K  F  G  G 190       200       210       220       230       240
GCAGCACTGTGAAATAGATAAGTCAAAAACCTGCTATGAGGGGAATGGTCACTTTTACCG
 Q  H  C  E  I  D  K  S  K  T  C  Y  E  G  N  G  H  F  Y  R 250       260       270       280       290       300
AGGAAAGGCCAGCACTGACACCATGGGCCGGCCCTGCCTGCCCTGGAACTCTGCCACTGT
 G  K  A  S  T  D  T  M  G  R  P  C  L  P  W  N  S  A  T  V 310       320       330       340       350       360
CCTTCAGCAAACGTACCATGCCCACAGATCTGATGCTCTTCAGCTGGGCTTGGGGAAACA
 L  Q  Q  T  Y  H  A  H  R  S  D  A  L  Q  L  G  L  G  K  H 370       380       390       400       410       420
TAATTACTGCAGGAACCCAGACAACCGGAGGCGACCCTGGTGCTATGTGCAGGTGGGCCT
 N  Y  C  R  N  P  D  N  R  R  R  P  W  C  Y  V  Q  V  G  L 430       440       450       460       470       480
AAAGCTGCTTGTCCAAGAGTGCATGGTGCATGACTGCGCAGATGGACAAAAGCCCTCCTC
 K  L  L  V  Q  E  C  M  V  H  D  C  A  D  G  Q  K  P  S  S 490       500       510       520       530       540
TCCTCCAGAAGAATTAAAATTTCAGTGTGGCCAAAAGACTCTGAGGCCTCAGTTTAAAAT
 P  P  E  E  L  K  F  Q  C  G  Q  K  T  L  R  P  Q  F  K  I 550       560       570       580       590       600
CATTGGCGGCGAATTCACCACCATCGAGAACCAGCCCTGGTTTGCGGCCATCTACAGGAG
 I  G  G  E  F  T  T  I  E  N  Q  P  W  F  A  A  I  Y  R  R
```

*Fig. 6a*

```
     610       620       630       640       650       660
GCACCGGGGGGGCTCTGTCACCTACGTGTGTGGAGGCAGCCTCATCAGCCCTTGCTGGGT
 H  R  G  G  S  V  T  Y  V  C  G  G  S  L  I  S  P  C  W  V 670       680       690       700       710       720
GATCAGCGCCACACACTGCTTCATTGATTACCCAAAGAAGGAGGACTACATCGTCTACCT
 I  S  A  T  H  C  F  I  D  Y  P  K  K  E  D  Y  I  V  Y  L 730       740       750       760       770       780
GGGTCGCTCAAGGCTTAACTCCAACACGCAAGGGGAGATGAAGTTTGAGGTGGAAAACCT
 G  R  S  R  L  N  S  N  T  Q  G  E  M  K  F  E  V  E  N  L 790       800       810       820       830       840
AATCCTACACAAGGACTACAGCGCTGACACGCTTGCTCACCACAACGACATTGCCCTTGCT
 I  L  H  K  D  Y  S  A  D  T  L  A  H  H  N  D  I  A  L  L 850       860       870       880       890       900
GAAGATCCGTTCCAAGGAGGGCAGGTGTGCGCAGCCATCCCGGACTATACAGACCATCTG
 K  I  R  S  K  E  G  R  C  A  Q  P  S  R  T  I  Q  T  I  C 910       920       930       940       950       960
CCTGCCCTCGATGTATAACGATCCCCAGTTTGGCACAAGCTGTGAGATCACTGGCTTTGG
 L  P  S  M  Y  N  D  P  Q  F  G  T  S  C  E  I  T  G  F  G 970       980       990       1000      1010      1020
AAAAGAGAATTCTACCGACTATCTCTATCCGGAGCAGCTGAAAATGACTGTTGTGAAGCT
 K  E  N  S  T  D  Y  L  Y  P  E  Q  L  K  M  T  V  V  K  L 1030      1040      1050      1060      1070      1080
GATTTCCCACCGGGAGTGTCAGCAGCCCCACTACTACGGCTCTGAAGTCACCACCAAAAT
 I  S  H  R  E  C  Q  Q  P  H  Y  Y  G  S  E  V  T  T  K  M 1090      1100      1110      1120      1130      1140
GCTGTGTGCTGCTGACCCACAGTGGAAAACAGATTCCTGCCAGGGAGACTCAGGGGGACC
 L  C  A  A  D  P  Q  W  K  T  D  S  C  Q  G  D  S  G  G  P 1150      1160      1170      1180      1190      1200
CCTCGTCTGTTCCCTCCAAGGCCGCATGACTTTGACTGGAATTGTGAGCTGGGGCCGTGG
 L  V  C  S  L  Q  G  R  M  T  L  T  G  I  V  S  W  G  R  G
```

*Fig. 6b*

```
         1210      1220      1230      1240      1250      1260
ATGTGCCCTGAAGGACAAGCCAGGCGTCTACACGAGAGTCTCACACTTCTTACCCTGGAT
  C  A  L  K  D  K  P  G  V  Y  T  R  V  S  H  F  L  P  W  I 1270      1280      1290      1300      1310      1320
CCGCAGTCACACCAAGGAAGAGAATGGCCTGGCCCTCTGAGGGTCCCCAGGGAGGAAACG
  R  S  H  T  K  E  E  N  G  L  A  L  *

1330      1340      1350      1360      1370      1380
GGCACCACCCGCTTTCTTGCTGGTTGCGATTTTGCAGTAGAGTCATCTCCATCAGCTGTA 1390      1400      1410      1420      1430      1440
AGAAGAGCTGGGAATATAGGCTCTGCACAGATGATTGCCTGTGCCACCGACCAGGGCGAA 1450      1460
CGACAATAGCTTTACCCTCACAAGCTT
```

*Fig. 6c*

```
        10         20         30         40         50         60
TCTAGATAAGGAGGTGAAAACCATGAACCAGGAACAGGTGTCTCCGTTGACTTTGCTTAA
                          M  N  Q  E  Q  V  S  P  L  T  L  L  K 70         80         90        100        110        120
GCTCCACCAGGTTCCGTCGAACTGTGACTGTCTAAATGGAGGAACATGTGTGTCCAACAA
 L  H  Q  V  P  S  N  C  D  C  L  N  G  G  T  C  V  S  N  K 130        140        150        160        170        180
GTACTTCTCCAACATTCACTGGTGCAACTGCCCAAAGAAATTCGGAGGGCAGCACTGTGA
 Y  F  S  N  I  H  W  C  N  C  P  K  K  F  G  G  Q  H  C  E 190        200        210        220        230        240
AATAGATAAGTCAAAAACCTGCTATGAGGGGAATGGTCACTTTTACCGAGGAAAGGCCAG
 I  D  K  S  K  T  C  Y  E  G  N  G  H  F  Y  R  G  K  A  S 250        260        270        280        290        300
CACTGACACCATGGGCCGGCCCTGCCTGCCCTGGAACTCTGCCACTGTCCTTCAGCAAAC
 T  D  T  M  G  R  P  C  L  P  W  N  S  A  T  V  L  Q  Q  T 310        320        330        340        350        360
GTACCATGCCCACAGATCTGATGCTCTTCAGCTGGGCTTGGGGAAACATAATTACTGCAG
 Y  H  A  H  R  S  D  A  L  Q  L  G  L  G  K  H  N  Y  C  R 370        380        390        400        410        420
GAACCCAGACAACCGGAGGCGACCCTGGTGCTATGTGCAGGTGGGCCTAAAGCTGCTTGT
 N  P  D  N  R  R  R  P  W  C  Y  V  Q  V  G  L  K  L  L  V 430        440        450        460        470        480
CCAAGAGTGCATGGTGCATGACTGCGCAGATGGAAAAAAGCCCTCCTCTCCTCCAGAAGA
 Q  E  C  M  V  H  D  C  A  D  G  K  K  P  S  S  P  P  E  E 490        500        510        520        530        540
ATTAAAAATTTCAGTGTGGCCAAAAGACTCTGAGGCCCCGCTTTAAGATTATTGGGGAGA
 L  K  F  Q  C  G  Q  K  T  L  R  P  R  F  K  I  I  G  G  E 550        560        570        580        590        600
ATTCACCACCATCGAGAACCAGCCCTGGTTTGCGGCCATCTACAGGAGGCACCGGGGGGG
 F  T  T  I  E  N  Q  P  W  F  A  A  I  Y  R  R  H  R  G  G
```

*Fig. 7a*

```
       610        620        630        640        650        660
CTCTGTCACCTACGTGTGTGGAGGCAGCCTCATCAGCCCTTGCTGGGTGATCAGCGCCAC
  S  V  T  Y  V  C  G  G  S  L  I  S  P  C  W  V  I  S  A  T 670        680        690        700        710        720
ACACTGCTTCATTGATTACCCAAAGAAGGAGGACTACATCGTCTACCTGGGTCGCTCAAG
  H  C  F  I  D  Y  P  K  K  E  D  Y  I  V  Y  L  G  R  S  R 730        740        750        760        770        780
GCTTAACTCCAACACGCAAGGGGAGATGAAGTTTGAGGTGGAAAACCTAATCCTACACAA
  L  N  S  N  T  Q  G  E  M  K  F  E  V  E  N  L  I  L  H  K 790        800        810        820        830        840
GGACTACAGCGCTGACACGCTTGCTCACCACAACGACATTGCCTTGCTGAAGATCCGTTC
  D  Y  S  A  D  T  L  A  H  H  N  D  I  A  L  L  K  I  R  S 850        860        870        880        890        900
CAAGGAGGGCAGGTGTGCGCAGCCATCCCGGACTATACAGACCATCTGCCTGCCCTCGAT
  K  E  G  R  C  A  Q  P  S  R  T  I  Q  T  I  C  L  P  S  M 910        920        930        940        950        960
GTATAACGATCCCCAGTTTGGCACAAGCTGTGAGATCACTGGCTTTGGAAAAGAGAATTC
  Y  N  D  P  Q  F  G  T  S  C  E  I  T  G  F  G  K  E  N  S 970        980        990       1000       1010       1020
TACCGACTATCTCTATCCGGAGCAGCTGAAAATGACTGTTGTGAAGCTGATTTCCCACCG
  T  D  Y  L  Y  P  E  Q  L  K  M  T  V  V  K  L  I  S  H  R 1030       1040       1050       1060       1070       1080
GGAGTGTCAGCAGCCCCACTACTACGGCTCTGAAGTCACCACCAAAATGCTGTGTGCTGC
  E  C  Q  Q  P  H  Y  Y  G  S  E  V  T  T  K  M  L  C  A  A 1090       1100       1110       1120       1130       1140
TGACCCACAGTGGAAAACAGATTCCTGCCAGGGAGACTCAGGGGGACCCCTCGTCTGTTC
  D  P  Q  W  K  T  D  S  C  Q  G  D  S  G  G  P  L  V  C  S 1150       1160       1170       1180       1190       1200
CCTCCAAGGCCGCATGACTTTGACTGGAATTGTGAGCTGGGGCCCGTGGATGTGCCCTGAA
  L  Q  G  R  M  T  L  T  G  I  V  S  W  G  R  G  C  A  L  K
```

*Fig. 7b*

```
        1210        1220       1230       1240       1250       1260
GGACAAGCCAGGCGTCTACACGAGAGTCTCACACTTCTTACCCTGGATCCGCAGTCACAC
  D   K   P   G   V   Y   T   R   V   S   H   F   L   P   W   I   R   S   H   T 1270       1280       1290       1300       1310       1320
CAAGGAAGAGAATGGCCTGGCCCTCTGAGGGTCCCCAGGGAGGAAACGGGCACCACCCGC
  K   E   E   N   G   L   A   L   *

1330       1340       1350       1360       1370       1380
TTTCTTGCTGGTTGCGATTTTGCAGTAGAGTCATCTCCATCAGCTGTAAGAAGAGCTGGG 1390       1400       1410       1420       1430       1440
AATATAGGCTCTGCACAGATGATTGCCTGTGCCACCGACCAGGGCGAACGACAATAGCTT

1450
TACCCTCACAAGCTT
```

*Fig. 7c*

```
         10        20        30        40        50        60
TCTAGATAAGGAGGTGAAAACCATGAACCAGGAACAGGTGTCTCCGTTGACTTTGCTTAA
                       M  N  Q  E  Q  V  S  P  L  T  L  L  K 70        80        90       100       110       120
GCTCCACCAGGTTCCGTCGAACTGTGACTGTCTAAATGGAGGAACATGTGTGTCCAACAA
 L  H  Q  V  P  S  N  C  D  C  L  N  G  G  T  C  V  S  N  K 130       140       150       160       170       180
GTACTTCTCCAACATTCACTGGTGCAACTGCCCAAAGAAATTCGGAGGGCAGCACTGTGA
 Y  F  S  N  I  H  W  C  N  C  P  K  K  F  G  G  Q  H  C  E 190       200       210       220       230       240
AATAGATAAGTCAAAAACCTGCTATGAGGGGAATGGTCACTTTTACCGAGGAAAGGCCAG
 I  D  K  S  K  T  C  Y  E  G  N  G  H  F  Y  R  G  K  A  S 250       260       270       280       290       300
CACTGACACCATGGGCCGGCCCTGCCTGCCCTGGAACTCTGCCACTGTCCTTCAGCAAAC
 T  D  T  M  G  R  P  C  L  P  W  N  S  A  T  V  L  Q  Q  T 310       320       330       340       350       360
GTACCATGCCCACAGATCTGATGCTCTTCAGCTGGGCTTGGGGAAACATAATTACTGCAG
 Y  H  A  H  R  S  D  A  L  Q  L  G  L  G  K  H  N  Y  C  R 370       380       390       400       410       420
GAACCCAGACAACCGGAGGCGACCCTGGTGCTATGTGCAGGTGGGCCTAAAGCTGCTTGT
 N  P  D  N  R  R  R  P  W  C  Y  V  Q  V  G  L  K  L  L  V 430       440       450       460       470       480
CCAAGAGTGCATGGTGCATGACTGCGCAGATGGAAAAAAGCCCTCCTCTCCTCCAGAAGA
 Q  E  C  M  V  H  D  C  A  D  G  K  K  P  S  S  P  P  E  E 490       500       510       520       530       540
ATTAAAATTTCAGTGTGGCCAAAAGACTCTGAGGCCTCAGTTTAAAATCATTGGCGGCGA
 L  K  F  Q  C  G  Q  K  T  L  R  P  Q  F  K  I  I  G  G  E 550       560       570       580       590       600
ATTCACCACCATCGAGAACCAGCCCTGGTTTGCGGCCATCTACAGGAGGCACCGGGGGGG
 F  T  T  I  E  N  Q  P  W  F  A  A  I  Y  R  R  H  R  G  G
```

*Fig. 8a*

```
      610       620       630       640       650       660
CTCTGTCACCTACGTGTGTGGAGGCAGCCTCATCAGCCCTTGCTGGGTGATCAGCGCCAC
  S  V  T  Y  V  C  G  G  S  L  I  S  P  C  W  V  I  S  A  T 670       680       690       700       710       720
ACACTGCTTCATTGATTACCCAAAGAAGGAGGACTACATCGTCTACCTGGGTCGCTCAAG
  H  C  F  I  D  Y  P  K  K  E  D  Y  I  V  Y  L  G  R  S  R 730       740       750       760       770       780
GCTTAACTCCAACACGCAAGGGGAGATGAAGTTTGAGGTGGAAAACCTAATCCTACACAA
  L  N  S  N  T  Q  G  E  M  K  F  E  V  E  N  L  I  L  H  K 790       800       810       820       830       840
GGACTACAGCGCTGACACGCTTGCTCACCACAACGACATTGCCTTGCTGAAGATCCGTTC
  D  Y  S  A  D  T  L  A  H  H  N  D  I  A  L  L  K  I  R  S 850       860       870       880       890       900
CAAGGAGGGCAGGTGTGCGCAGCCATCCCGGACTATACAGACCATCTGCCTGCCCTCGAT
  K  E  G  R  C  A  Q  P  S  R  T  I  Q  T  I  C  L  P  S  M 910       920       930       940       950       960
GTATAACGATCCCCAGTTTGGCACAAGCTGTGAGATCACTGGCTTTGGAAAAGAGAATTC
  Y  N  D  P  Q  F  G  T  S  C  E  I  T  G  F  G  K  E  N  S 970       980       990      1000      1010      1020
TACCGACTATCTCTATCCGGAGCAGCTGAAAATGACTGTTGTGAAGCTGATTTCCCACCG
  T  D  Y  L  Y  P  E  Q  L  K  M  T  V  V  K  L  I  S  H  R 1030      1040      1050      1060      1070      1080
GGAGTGTCAGCAGCCCCACTACTACGGCTCTGAAGTCACCACCAAAATGCTGTGTGCTGC
  E  C  Q  Q  P  H  Y  Y  G  S  E  V  T  T  K  M  L  C  A  A 1090      1100      1110      1120      1130      1140
TGACCCACAGTGGAAAACAGATTCCTGCCAGGGAGACTCAGGGGGACCCCTCGTCTGTTC
  D  P  Q  W  K  T  D  S  C  Q  G  D  S  G  G  P  L  V  C  S 1150      1160      1170      1180      1190      1200
CCTCCAAGGCCGCATGACTTTGACTGGAATTGTGAGCTGGGGCCGTGGATGTGCCCTGAA
  L  Q  G  R  M  T  L  T  G  I  V  S  W  G  R  G  C  A  L  K
```

*Fig. 8b*

```
      1210        1220       1230       1240       1250       1260
GGACAAGCCAGGCGTCTACACGAGAGTCTCACACTTCTTACCCTGGATCCGCAGTCACAC
  D  K  P  G  V  Y  T  R  V  S  H  F  L  P  W  I  R  S  H  T 1270        1280       1290       1300       1310       1320
CAAGGAAGAGAATGGCCTGGCCCTCTGAGGGTCCCCAGGGAGGAAACGGGCACCACCCGC
  K  E  E  N  G  L  A  L  *

1330        1340       1350       1360       1370       1380
TTTCTTGCTGGTTGCGATTTTGCAGTAGAGTCATCTCCATCAGCTGTAAGAAGAGCTGGG 1390        1400       1410       1420       1430       1440
AATATAGGCTCTGCACAGATGATTGCCTGTGCCACCGACCAGGGCGAACGACAATAGCTT

1450
TACCCTCACAAGCTT
```

*Fig. 8c*

EFFECTIVE THROMBOSIS MEDIATED BY HUMAN PROUROKINASE-LIKE POLYPEPTIDES WITH INCREASED BINDING AFFINITY FOR THROMBOSIS

FIELD OF THE INVENTION

This invention relates to methods for the preparation of human prourokinase-like polypeptides i.e., substantially pure human prourokinase mutein, with binding ability through covalent bonds with blood clots, by means of gene engineering. Prourokinase mutein functions as a thrombolytic agent.

DESCRIPTION OF RELATED ART

Human urokinase is an enzyme present in human urine in a trace amount, and can convert the inactive plasminogen to the active plasmin. The formed plasmin can lyse blood clots. Owing to this fact, human urokinase is clinically used widely as a thrombolytic agent.

However, human urokinase has low affinity with blood clot and is of the active form. Therefore it activates not only plasminogen at or in the vicinity of the blood clot but also plasminogen in the circulation, resulting in formation of a large amount of plasmin in the circulation. The extensive plasmin formation in the circulation modifies platlet function (Blood: Vol. 68, p 275, 1986) and degrades circulating fibrinogen and clotting factors V and VIII (Blood: Vol. 68, p 1280, 1986) the extensive plasmin formation also carried the risk of grave side effect of systemic hemorrhage, which often results in death (Journal of American Colleague Cardiology: Vol. 10, p 970, 1987).

The ideal thrombolytic agent should be capable of attacking the components of a thrombus while sparing the circulating clotting proteins and platlets and have an appropriate half life in vivo. In recent years, human prourokinase and tissue plasminogen activator (hereinafter referred to as tPA) are under development as the second generation thrombolytic agents. These agents activate the plasminogen praticularlly in close proximity to a thrombus. Therefore, excessive administration of these thrombolytic agents carries less risk of grave side effect of systemic hemorrhage. However, human prourokinase has better affinity with thrombus than human urokinase, but has not yet been shown to be of practical interest. The tPA has such defects as a large amount of inhibitor (plasminogen activator inhibitor I) present in the blood, a short half life so that therapeutic effects are not realized unless a large amount is administered, and an occurrence of reocclusion after artery recanalization by thrombolysis in many cases (Circulation: Vol. 73, p 347, 1986; New England Journal of Medicine: Vol. 317, p 581, 1987). Substances which are not inactivated irreversibly by plasminogen activator inhibitor I and which have better affinity with blood clot than human prourokinase are believed to be ideal thrombolytic agents. Attempts have been made to produce such substances.

A first of such substances is a chimeric substance in which the NH2-terminal region of tPA is fused with the COOH-terminal region of human prourokinase having an enzymatic activity to activate the plasminogen, and produced by recombinant DNA technology, with recognition that the NH2-terminal region of tPA has high affinity with the blood clot (The Journal of Biological Chemistry, Vol. 268, p 10855, 1987; Thrombosis and Haemostasis, Vol. 54, p 893, 1985). However, contrary to the expectation, this substance has less affinity to blood clot as that of tPA.

A second of the substances is a chimeric substance in which about 560 amino acids at the NH2-terminal side which has affinity to the blood clot is combined chemically with the COOH-terminal region of human prourokinase, same as that described above (Biochemistry, Vol. 25, p 3603, 1986). A third is a chimeric substance made by chemically combining an antibody against fibrin which is a major component of blood clot, with the COOH-terminal region of human prourokinase, same as that described above (Clinical Research Abstract, Vol. 36, p 265A, 1989). The second and third substances have improved affinity to blood clot; therefore, there substances would be expected to improve the thrombolytic effect. Economical manufacturing of these second and third substances is however difficult.

Further, urokinase derivatives are reported (PCT/SU84/00008:WO84/04536) and such derivatives bind with fibrin through fibrinogen chemically linked to urokinase beforehand. Further more, it is reported that an oligopeptide forms covalent bonds with fibrin enzymatically due to the action of blood coagulation factor XIII and it is suggested that affinity of urokinase with blood clot is improved by bonding such oligopeptide with urokinase (PCT/US88/02276: WO89/00051). However the inventors of this application recognized in their study that affinity of urokinase with blood clot is scarcely improved by bonding such oligopeptide with urokinase.

The purpose of this invention is human prourokinase-like polypeptides with better affinity to blood clot than that of human prourokinase, and is to provide a method to prepare the said polypeptides economically.

SUMMARY OF THE INVENTION

This invention is human prourokinase-like polypeptides (which hereinafter may be referred to as the human prourokinase-like polypeptides i.e., human prourokinase mutein of this invention) made by adding an oligopeptide having a structure to form a covalent bonds with blood clot through enzymatic action of the human blood coagulation factor XIII (which hereinafter may be referred to as the oligopeptide(s)), to the NH2-terminal side of a human prourokinase derivative (which hereinafter may be referred to as the human prourokinase derivative(s)).

BRIEF DESCRIPTION OF THE DRAWINGS

FIG. 5 illustrates the DNA base sequence and corresponding amino acid sequence for encoding the human prourokinase-like polypeptide described as FCUK (-,q).

FIG. 6 illustrates the DNA base sequence and corresponding amino acid sequence for encoding the human prourokinase-like polypeptide described as AHUK (q.q).

FIG. 7 illustrates the DNA base sequence and corresponding amino acid sequence for encoding the human prourokinase-like polypeptide described as APUK (k,k).

FIG. 8 illustrates the DNA base sequence and corresponding amino acid sequence for encoding the human prourokinase-like polypeptide described as APUK (k,q).

Figure 1:
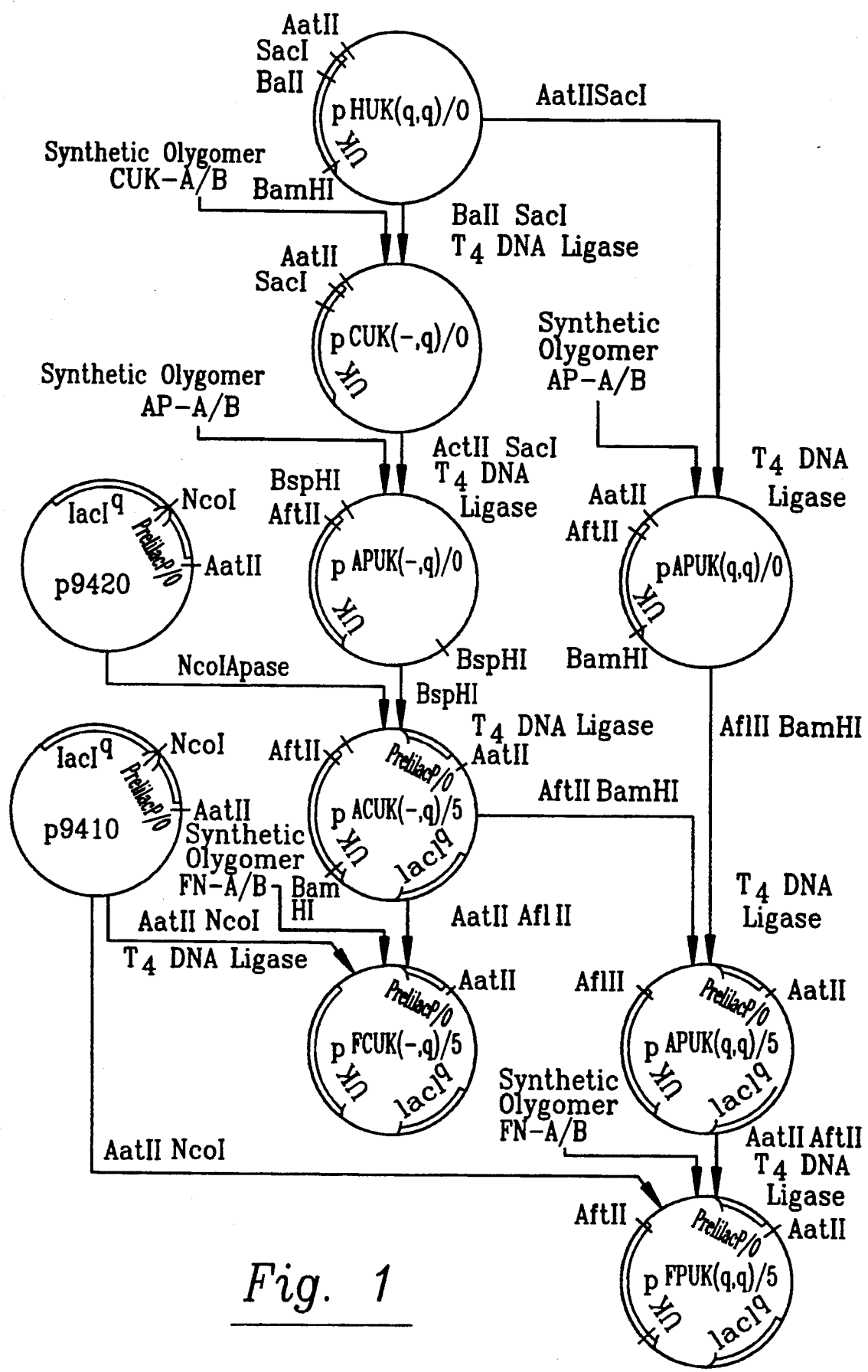
FIG. 1 is a schematic diagram for the preparation of plasmid as in Example 1 and in Example 2.

fibrinogen γ-chain, α2.antiplasmin and fibronectin, as can be seen from the board object of this invention.

The following are examples of preferable oligopeptides which are useful in the practice of this invention.

| Name of the oligopeptide | Amino acid sequence |
|---|---|
| A | (Met.)Asn.Gln.Glu.Gln.Val.Ser.Pro.Leu.Thr.Leu.Leu.Lys. |
| F | (Met.)Gln.Ala.Gln.Gln.Met.Val.Gln.Pro.Gln.Ser.Pro.Val.Ala.Val.Lys. |
| $V_1$ | (Met.)Ala.Gln.Lys.Met.Val.Gln.Pro.Leu.Thr.Leu.Leu.Lys. |
| $V_2$ | (Met.)Ala.Gln.Lys.Met.Val.Gln.Pro.Gln.Thr.Leu.Leu.Lys. |
| $V_3$ | (Met.)Gln.Glu.Gln.Val.Ser.Pro.Gln.Thr.Leu.Leu.Lys. |
| $V_4$ | (Met.)Asn.Gln.Asp.Gln.Val.Ser.Pro.Gln.Thr.Leu.Leu.Lys. |
| $V_5$ | (Met.)Asn.Gln.Glu.Asn.Val.Ser.Pro.Gln.Thr.Leu.Leu.Lys. |
| $V_6$ | (Met.)Asn.Gln.ser.Met.val.ser.Pro.Gln.Thr.Leu.Leu.Lys. |

DESCRIPTION OF THE PREFERRED EMBODIMENTS

This invention is described in detail.

(A) The oligopeptides

As used in this invention, the oligopeptides are substances capable of forming covalent bonds with fibrin, a major component in the blood clot, in a human body. The inventors studied the details of the amino acid sequences of α2.antiplasmin, fibronectin and fibrinogen γ-chain, which are representatives of the said substances, and found that the structure of the sequence of several e.g., 10 amino acids at the NH2-terminal side is ... Gln◯◯Val (or Leu)◯Pro(or Gly) ... (where ◯ stands for an amino acid) and discovered that a peptide with such an amino acid sequence has the capability of forming covalent bonds with such components as fibrin through the enzymatic action of human blood coagulation factor XIII (active form). Thus this invention has been completed.

The oligopeptide may be any oligomer with a structure having the ability to form covalent bonds with a blood clot through the enzymatic action of blood coagulation factor XIII (active form). Concrete examples are those with the structure of ... Gln◯◯Val (or Leu)◯Pro(or Gly) ... The oligopeptide is not limited to oligopeptides at the NH2-terminal side of each of where (Met) is methionine which may be present in some cases.

(B) The human prourokinase derivatives

The human prourokinase derivatives include (i) those that do not contain the whole amino acid sequences of human prourokinase, (ii) those containing amino acid sequences of the region necessary and sufficient to exhibit the enzymatic action for activating plasminogen (for instance, those with defect of from the first serine to the third glutamic acid or from the first serine to the 143th glutamic acid of the amino acid sequence of human prourokinase) and (iii) those in which part of the amino acids is changed to a desirable form [for instance, those of which one or both of the 135th lysine and 156th arginine are changed to an amino acid other than basic amino acid (e.g. glutamic acid); and those whose 157th phenylalanine is changed to an acidic amino acid (e.g. aspartic acid)].

(C) The human prourokinase-like polypeptides of this invention

The human prourokinase-like polypeptides of this invention can be produced by combining the human prourokinase derivatives and the oligopeptides. Preferable examples are shown below in parallel to the amino acid sequence of natural human prourokinase. The amino acid sequence is illustrated only by portions different from the amino acid sequence of natural human prourokinase and the amino acid sequence in their region by one letter abbreviation.

|  | amino acid sequence |
|---|---|
| NATURAL HUMAN PROUROKINASE | 1　　　　　　135　　　　144<br>SNELHQVP ... GKKPSSPPEELKQC<br>156<br>... RPRFKIIGG ... |
|  | HUMAN PROUROKINASE-LIKE POLYPEPTIDES: |
| AHUK(q,q) | (M)NQEQVSPLTLLKLSNELHQVP ... GQKPSSPPEELKFQC<br>... RPQFKIIGG ... |
| APUK(q,q) | (M)NQEQVSPLTLLKLHQVP ... GQKPSSPPEELKFQC<br>... RPQFKIIGG ... |
| APUK(k,q) | (M)NQEQVSPLTLLKLHQVP ... GKKPSSPPEELKFQC<br>... RPQFKIIGG ... |
| APUK(k,d) | (M)NQEQVSPLTLLKLHQVP ... GKKPSSPPEELKFQC<br>... RPRDKIIGG ... |
| APUK(k,k) | (M)NQEQVSPLTLLKLHQVP ... GKKPSSPPEELKFQC<br>... RPRFKIIGG ... |
| FPUK(q,q) | (M)QAQQMVQPQSPVAVKLHQVP ... GQKPSSPEELKFQC<br>... RPQFKIIGG ... |
| $V_1$PUK(k,q) | (M)AQKMVGPLTLLKLHQVP ... GKKPSSPPEELKFQC<br>... RPQFKIIGG ... |
| $V_2$PUK(k,q) | (M)AQKMVGPQTLLKLHQVP ... GKKPSSPPEELKFQC<br>... RPQFKIIGG ... |
| ACUK(-,q) | (M)NQEQVSPLTLLKLKFQC<br>... RPQFKIIGG ... |

| | -continued |
|---|---|
| FCUK(-,q) | (M)QAQQMVQPQSPVAVKLKFQC<br>... RPQFKIIGG ... | where (M) is methionine which may be present in some cases.

(D) Gene system of the human prourokinase-like polypeptides of this invention and their preparation method The DNA segment encoding the human prourokinase-like polypeptides of this invention consists of the product formed by linking a DNA encoding the amino acid sequence of oligopeptide with a structure having the ability to form covalent bond with a blood clot (such as fibrin of a major component) through the enzymatic action of human blood coagulation factor XIII (active form) (hereinafter referred to the oligopeptide), with a DNA encoding the amino acid sequence of the human prourokinase derivative.

The DNA encoding the amino acid sequence of the oligopeptide is a DNA of continuously bound codons, each of which encodes an amino acid. All amino acid codons are applicable as the codons. Codons which are easily expressed in a host cell are preferably used, and also the use of codons which do not form a folded structure at the level of messenger RNA due to the series of these codons is preferable. Such DNA segments are designed in a desirable form which can be easily prepared by chemical synthesis.

Examples of preferable DNA segments encoding the oligopeptides are described which A human prourokinase-like polypeptide of this invention from which the first serine to the third glutamic acid are deleted is accumulated in *E. coli* cells in a larger amount than human prourokinase with no amino acids deleted.

Examples of the preferred human prourokinase derivatives are described, as follows.

(1) Derivatives in which the codon encoding the second to eighth amino acids from the $NH_2$-terminal side of the amino acid sequence of natural human prourokinase is a codon described in 1 below (in the case of human prourokinase with defect of the first to third amino acids, the codon encoding the amino acids of the fourth Leu to the eighth Pro):

1. $Asn^2$ .$Glu^3$ .$Leu^4$ .$His^5$ .$Gln^6$ .$Val^7$ .$Pro^8$
AAC. GAG. CTC. CAC. CAG. GTT. CCG (2) In the case of a human prourokinase derivatives with defect from the first serine to 143th glutamic acid, derivatives in which the codon encoding leucine and lysine corresponding to the 144th and 145th is a codon described in 2 below:

2. $Leu^{144}$ .$Lys^{145}$
CTC. AAG

| Code | |
|---|---|
| A Amino acid sequence: | (Met)Asn.Gln.Glu.Gln.Val.Ser.Pro.Leu.Thr.Leu.Leu.Lys. |
| DNA | ATG.AAC.CAG.GAA.CAG.GTG.TCT.CCG.TTG.ACT.TTG.CTT.AAG. |
| F Amino acid sequence: | (Met)Gln.Ala.Gln.Gln.Met.Val.Gln.Pro.Gln.Ser.Pro.Val. |
| DNA | ATG.CAG.GCA.CAA.CAG.ATG.GTT.CAA.CCT.CAG.TCA.CCG.GTT.<br>Ala.Val.Lys.<br>GCT.GTT.AAG. |
| $V_1$ Amino acid sequence: | (Met)Ala.Gln.Lys.Met.Val.Gln.Pro.Leu.Thr.Leu.Leu.Lys. |
| DNA | ATG.GCA.CAA.AAA.ATG.GTT.CAG.COG.CTG.ACC.TTG.CTT.AAG. |
| $V_2$ Amino acid sequence: | (Met)Ala.Gln.Ly.Met.Val.Gln.Pro.Gln.Thr.Leu.Leu.Lys. |
| DNA | ATG.GCA.CAA.AAA.ATG.GTT.CAG.CCG.CAA.ACT.CTT.CTT.AAG. |
| $V_3$ Amino acid sequence: | (Met).Gln.Glu.Gln.Val.Ser.Pro. |
| DNA | ATG CAG GAA CAG GTG TCT CCG<br>Gln.Thr.Leu.Leu.Lys.<br>CAG ACT TTG CTT AAG |
| $V_4$ Amino acid sequence: | (Met).Asn.Gln.Asp.Gln.Val.Ser. |
| DNA | ATG AAC CAG GACCAG GTG TCT<br>Pro.Gln.Thr.Leu.Leu.Lys.<br>CCG CAG ACT TTG CTT AAG |
| $V_5$ Amino acid sequence: | (Met).Asn.Gln.Glu.Asn.Val.Ser. |
| DNA | ATG AAC CAG GAA AAC GTG TCT<br>Pro.Gln.Thr.Leu.Leu.Lys.<br>CCG CAG ACT TTG CTT AAG |
| $V_6$ Amino acid sequence: | (Met).Asn.Gln.Ser.Met.Val.Ser. |
| DNA | ATG AAC CAA TCT ATGGTG TCT<br>Pro.Gln.Thr.Leu.Leu.Lys.<br>CCG CAG ACT TTG CTT AAG | where (Met) is methionine which may be present in some cases.

A DNA segment encoding the human prourokinase derivative is obtained from DNA encoding natural human prourokinase. In this case, more preferable results are obtained if a DNA encoding natural human prourokinase is changed to a codon which is easily expressed in the host cell used or to a codon which does not form a folded structure at the level of messenger RNA, though the DNA can be used as it is.

(3) In the case of a mutein in human prourokinase derivatives whose 156th arginine is changed to glutamine, derivatives of which the codon encoding the amino acids form the 156th glutamine to 162th glycine is a codon described in 3, below 3. $Gln^{156}$ .$Phe^{157}$ .$Lys^{158}$ .$Ile^{159}$ .$Ile^{160}$ .$Gly^{161}$ .$Gly^{162}$
CAG. TTT. AAA. ATC. ATT. GGC. GGC The DNA fragment encoding the human prourokinase-like polypeptides of this invention can be inserted to the expression plasmid. Concrete DNA base sequence and corresponding amino acid sequence are shown in FIG. 5 (FCUK(−,q)), FIG. 6 (AHUK(q,q)), FIG. 7 (APUK(k,k)) and FIG. 8 (APUK(k,q)). The intended product is accumulated in the host cell or in the culture solution by culturing the transformant (host cell) transformed by the transduction of the expression plasmid. When E. coli is used as a host cell, the intended product is typically obtained as an insoluble precipitate after cell disruption by such means as ultrasonication or Gaulin homogenizer.

The precipitate is dissolved in an aqueous solution such as of guanidine hydrochloride or urea, and then oxidized by air in the presence of a thiol compound in order to reconstruct the original steric structure of the intended product. It is then purified, for example by fractional precipitation by salting out with ammonium sulfate, hydrophobic chromatography, or metal chelate chromatography. Generally employed biochemical purification technologies other than the above can be applied.

The human pruorokinase-like polypeptides of this invention are thus prepared with economical advantage.

This invention is further described in detail by reference to the following examples. The operative conditions including restriction enzymes, isolation methods of DNA fragments and synthesized double strand DNAs used in the examples are described below:

(1) Reaction of each restriction enzyme

Into 50 μl of each of the following reaction solutions containing 1 μg of DNA (plasmid or DNA fragment) was added 10 units of each restriction enzyme, and the solutions were incubated at a relevant temperature described below for two hours. When partial digestion was carried out, 1 to 2 units of restriction enzyme was added and the solutions were incubated for 0.5 to an hour.

(2) Blunting reaction of DNA with T$_4$ DNA polymerase

Into 50 μl of the following reaction solution containing 1 to 2 μg of linear DNA was added 0.5 to 1 unit of T$_4$ DNA polymerase to incubate at 37° C. for an hour.
Composition of reaction solution:
67 mM of Tris hydrochloric acid (pH 8.8), 6.7 mM of MgCl$_2$, 16.6 μM of (NH$_4$)$_2$ SO$_4$, 10 mM of β-mercaptoethanol, 6.7 μM of ethylenediaminetetraacetic acid, 0.0167% of bovine serum albumin, 330 μM of dCTP, 330 μM of daTP, 330 μM of dGTP and 330 μM of dTTP.

(3) Blunting reaction of DNA with Klenow fragment

Into 50 μl of the following reaction solution containing 1 to 2 μg of linear DNA was added 0.5 to 1 unit of Klenow fragment to incubate at 25° C. for an hour.
Composition of reaction solution:
67 mM of potassium phosphate buffer (pH 7.4), 6.7 mM of MgCl$_2$, 1 mM of β-mercaptoethanol, 33 μM of dATP, 33uμM of dTTP, 33 μM of dGTP and 33 μM of dCTP.

(4) Ligation reaction of DNA by T$_4$ DNA ligase

Into 7.5 μl of DNA solution containing (about 0.1 μg of) DNA fragment to be ligated were mixed 60 μl of solution A of "DNA ligation kit" made by Takara Shuzo Co. and 7.5 μl of Solution B of the same (containing T$_4$ DNA ligase) to incubate at 16° C. for 30 minutes.

(5) Isolation of DNA fragment and others

After each plasmid was digested with restriction enzyme, the intended DNA fragment was isolated by agarose electrophoresis. The DNA fragment obtained by electric elution was extracted with phenol and chloroform, and purified by precipitation with ethanol. E. coli JM103 strain was transformed by each plasmid prepared. The transformant was investigated by quick isolation method by alkaline lysis, and a clone with the intended plasmid was obtained.

(6) Synthesized double helical DNA

The synthesized double strand DNAs used to prepare an intended plasmid were produced according to the

| restriction enzyme name | Composition of reaction solution (m mole) | | | | | | reaction temperature (°C.) |
|---|---|---|---|---|---|---|---|
| | Tris-hydrochloric acid buffer (pH) | | NaCl (KCl) | MgCl$_2$ | mercaptoethanol (dithio threitol) | bovine serum albumin (%) | |
| Aat II | 10 | (7.5) | (50) | 10 | 1 | — | 37 |
| Acc III | 10 | (8.5) | 200 | 7 | 7 | — | 60 |
| Axy I | 10 | (7.5) | 100 | 7 | 7 | — | 37 |
| Afl II | 10 | (8.0) | (40) | 7 | 7 | 0.01 | 37 |
| Bal I | 20 | (8.5) | — | 7 | 7 | 0.01 | 37 |
| BamH I | 6 | (7.9) | 150 | 6 | — | — | 30 |
| Ban II | 6 | (7.4) | 50 | 6 | 10 | — | 37 |
| BspH I | 10 | (7.4) | (100) | 10 | — | 0.01 | 37 |
| Dra II | 10 | (8.0) | (40) | 7 | 7 | — | 37 |
| EcORI | 100 | (7.5) | 50 | 5 | — | — | 37 |
| Eco47 III | 10 | (8.5) | (80) | 7 | 7 | 0.01 | 37 |
| Hind III | 10 | (7.5) | 60 | 7 | — | — | 37 |
| Kpn I | 10 | (7.5) | — | 7 | 7 | — | 37 |
| Nar I | 6 | (7.4) | — | 6 | 6 | — | 37 |
| Nae I | 10 | (8.0) | 20 | 1 | 6 | 0.01 | 37 |
| Nco I | 10 | (8.5) | 80 | 7 | — | 0.01 | 37 |
| Pst I | 10 | (7.5) | 100 | 10 | — | — | 37 |
| Sca I | 6 | (7.4) | 100 | 6 | (1) | — | 37 | following procedure: Each single chain DNA oligomer was synthesized by amidite method, purified by OPC cartridge (Applied Biosystem Co.), and dried. Each pair of isolated DNA was dissolved in a buffer (pH 7.6) of 20 mM of Tris-hydrochloric acid and 10 mM of MgCl$_2$, heated at 95° C. for 2 minutes, gradually cooled down to room temperature, and then kept at 12° C. for over night to anneal. The double strand DNAs described below were thus obtained:

| Name of the Synthesize double helical DNA | |
|---|---|
| HL-A | 5'-TTAAGCTGAGCAACGAGCT-3' |
| HL-B | 3'-CGACTCGTTGC-5'= |
| CUK-A | 5'-CAAGTTTCAGTGTGG-3' |
| CUK-B | 3'-TCGAGTTCAAAGTCACACC-5' |
| AP-A | 5'-CATGAACCAGGAACAGGTGTCTCCGTTGACTTTGCTTAAGCT-3' |
| AP-B | 3'-TGCAGTACTTGGTCCTTGTCCACAGAGGCAACTGAAACGAAT-5' |
| FN-A | 5'-CATGCAGGCACAACAGATGGTTCAACCTCAGTCACCGGTTGCTG-3' |
| FN-B | 3'-GTCCGTGTTGTCTACCAAGTTGGAGTCAGTGGCCAACGACAATT-5' |
| V$_1$-A | 5'-CATGGCACAAAAAATGGTTCAGCCGCTGACCTTGC-3' |
| V$_1$-B | 3'-CGTGTTTTTTACCAAGTCGGCGACTGGAACGAATT-5' |
| V$_2$-A | 5'-CATGGCACAAAAAATGGTTCAGCCGCAAACTCTTC-3' |
| V$_2$-B | 3'-CGTGTTTTTTACCAAGTCGGCGTTTGAGAAGAATT-5' |
| V$_3$-A | 5'-CATGCAGGAACAGGTGTCTCCGCAGACTTTGCTTAAGCT-3' |
| V$_3$-B | 3'-TGCAGTACGTCCTTGTCCACAGAGGCGTCTGAAACGAAT-5' |
| V$_4$-A | 5'-CATGAACCAGGACCAGGTGTCTCCGCAGACTTTGCTTAAGCT-3' |
| V$_4$-B | 3'-TGCAGTACTTGGTCCTGGTCCACAGAGGCGTCTGAAACGAAT-5' |
| V$_5$-A | 5'-CATGAACCAGGAAAACGTGTCTCCGCAGACTTTGCTTAAGCT-3' |
| V$_5$-B | 3'-TGCAGTACTTGGTCCTTTTGCACAGAGGCGTCTGAAACGAAT-5' |
| V$_6$-A | 5'-CATGAACCAATCTATGGTGTCTCCGCAGACTTTGCTTAAGCT-3' |
| V$_6$-B | 3'-TGCAGTACTTGGTTAGATACCACAGAGGCGTCTGAAACGAAT-5' |
| TUK1-A | 5'-GCCTCAGTTTAAAATCATTGGCGGCG-3' |
| TUK1-B | 3'-AGTCAAATTTTAGTAACCGCCGCTTA-5' |
| TUK2-A | 5'-GCCTCGCGATAAAATCATTGGCGGCG-3' |
| TUK2-B | 3'-AGCGCTATTTTAGTAACCGCCGCTTAA-5' |
| CROSD-A | 5'-CTAGATAAGGAGGTGAAAACCATG-3' |
| CROSD-B | 3'-TATTCCTCCACTTTTGGTAC-5' |

EXAMPLE 1

Preparation of plasmid pACUK (−,q)/5, plasmid pFCUK (−,q)/5, plasmid pV$_1$PUK (k,q)/5 and plasmid pV$_2$PUK (k,q)/5

About 3.9 kb of DNA fragment isolated after plasmid pHUK (q,q)/0 was digested with restriction enzymes Bal I and Sac I and synthesized oligomer CUK-A/B were linked by T$_4$DNA ligase to give plasmid pCUK (−,q)/0.

About 3.9 kb of DNA fragment isolated after plasmid pCUK (−,q)/0 was digested with restriction enzymes Aat II and Sac I and synthesized oligomer AP-A/B were linked by T$_4$DNA ligase to give plasmid pACUK (−, q)/0.

Plasmid p9420 was digested with restriction enzyme Nco I and treated with alkaline phosphatase and a DNA fragment containing urokinase gene which was isolated after plasmid pACUK (−,q)/0 was digested with restriction enzyme BspH I were linked by T$_4$DNA ligase to give plasmid pACUK (−,q)/5.

About 5.4 kb of DNA fragment isolated after plasmid pACUK (−,q)/5 was digested with restriction enzymes Aat II and Afl II, about 0.5 kb of DNA fragment isolated after plasmid p9410 was digested with restriction enzymes Aat II and Nco I, and synthesized oligomer FN-A/B were linked by T$_4$DNA ligase to give plasmid pFCUK (−,q)/5.

About 5.8 kb of DNA fragment isolated after plasmid pAPUK (k,q)/5 was digested with restriction enzymes Aat II and Afl II, about 0.5 kb of DNA fragment isolated after plasmid p9410 was digested with restriction enzymes Aat II and Nco I, and synthesized oligomer V$_1$-A/B were linked by T$_4$DNA ligase to give plasmid pV$_1$PUK (k,q)/5.

About 5.8 kb of DNA fragment isolated after plasmid pAPUK (k,q)/5 was digested with restriction enzymes Aat II and Afl II, about 0.5 kb of DNA fragment isolated after plasmid p9410 was digested with restriction enzymes Aat II and Nco I, and synthesized oligomer V$_2$-A/B were linked by T$_4$DNA ligase to give plasmid PV$_2$PUK (k, g/5.

EXAMPLE 2

Preparation of plasmid pAPUK (q,q)/5 and plasmid pFPUK (q,q)/5

About 5.3 kb of DNA fragment isolated after plasmid pHUK (q,q)/0 was digested with restriction enzymes Aat II and Sac I and synthesized oligomer AP-A/B were linked by T$_4$DNA ligase to give plasmid pAPUK (q,q)/0.

About 1.2 kb of DNA fragment isolated after plasmid pAPUK (q,q)/0 was digested with restriction enzymes Afl II and BamH I and about 5.1 kb of DNA fragment isolated after plasmid pACUK (−,q)/5 was digested with restriction enzymes Afl II and BamH I were linked by T$_4$DNA ligase to give plasmid pAPUK (q,q)/5.

About 5.8 kb of DNA fragment isolated after plasmid pAPUK (q,q)/5 was digested with restriction enzymes Aat II and Afl II, about 0.5 kb of DNA fragment isolated after plasmid p9410 was digested with restriction enzymes Aat II and Nco I and synthesized oligomer FN-A/B were linked by T$_4$DNA ligase to give plasmid pFPUK (q,q)/5.

EXAMPLE 3

Preparation of plasmid pAHUK (q,q)/5, plasmid pAPUK (k,k)/5, plasmid pAPUK (k,q)/5 and plasmid pAPUK (k,d)/5

About 4.9 kb of DNA fragment isolated after plasmid pAPUK (q,q)/5 was digested with restriction enzymes Afl II and BamH I, about 1.4 kb of DNA fragment isolated after plasmid pHUK (q,q)/0 was digested with restriction enzymes BamH I and Sac I and synthesized oligomer HL-A/B were linked by T4DNA ligase to give plasmid pAHUK (q,q)/5.

E. coli HB101 containing plasmid pAHUK (q,q)/5 is deposited as FERM BP-2467 to the Fermentation Research Institute, Agency of Industrial Science & Technology, Ministry of International Trade and Industry.

About 5.2 kb of DNA fragment isolated after plasmid pAPUK (q,q)/5 was digested with restriction enzymes Hind III and Pst I and about 1.1 kb of DNA fragment isolated after plasmid pMUT4H was digested with restriction enzymes Hind III and Pst I were linked by T4DNA ligase to give plasmid pAPUK (k,k)/5.

E. coli HB101 containing plasmid pAPUK (k,k)/5 is deposited as FERM BP-2465 to the Fermentation Research Institute, Agency of Industrial Science & Technology, Ministry of International Trade and Industry.

About 5.5 kb of DNA fragment isolated after plasmid pAPUK (k,k)/5 was digested with restriction enzymes Bal I and BamH I and about 0.75 kb of DNA fragment isolated after plasmid pCUK (−,q)/0 was digested with restriction enzymes Bal I and BamH I were linked by T4DNA ligase to give plasmid pAPUK (k,q)/5.

E. coli HB101 containing plasmid pAPUK (k,q)/5 is deposited as FERM BP-2466 to the Fermentation Research Institute, Agency of Industrial Science & Technology, Ministry of International Trade and Industry.

About 5.5 kb of DNA fragment isolated after plasmid pAPUK (k,k)/5 was digested with restriction enzymes Bal I and BamH I and about 0.75 kb of DNA fragment isolated after plasmid pHUK (q,d)/0 was digested with restriction enzymes Bal I and BamH I were linked by T4DNA ligase to give plasmid pAPUK (k,d)/5.

EXAMPLE 4

Expression of human prourokinase-like polypeptides gene by E. coli

Plasmids pAHUK (q,q)/5, pAPUK (q,q)/5, pAPUK (k,q)/5, pAPUK (k,d)/5, pAPUK (k,k)/5, pFPUK (q,q)/5, pACUK (−,q)/5, pFCUK (−,q)/5, pV1PUK (k,q)/5 and pV2PUK (k,q)/5, which were obtained in Examples 1, 2 and 3, were each transformed to E. coli JM103 strain according to a usual method. Each of the obtained transformants was cultured aerobically in 50-ml of L-broth at 37° C. When the absorbance at 600 nm became about 1.0, 0.5 ml of 100 mM isopropyl thiogalactopyranoside (IPTG) was added, and culture was continued for another 4 hours to express each human prourokinase-like polypeptide gene.

EXAMPLE 5

Extraction and purification of gene products from E. coli 10 g of each of wet cells obtained in Example 4 was suspended in 100 ml of 10 mM glycine-NaOH buffer (pH 9.0, and containing 0.1M of NaCl and 5 mM of EDTA), to which 50 mg of lysozyme was added and stirred for an hour while cooled with ice. Then the cells were disrupted by ultrasonication. Immediately after the disruption, the cells were centrifuged at 4° C. and 12,000 rpm for 30 minutes to give precipitate. The obtained precipitate was washed with 10 mM glycine-NaOH buffer (pH 9.0) several times, and dissolved with stirring in a solution of 500 ml of 0.1M glycine-NaOH buffer (pH 9.0) to which 500 ml of 8M guanidine hydrochloride was added. Deionized water, 1M glycine-NaOH buffer (pH 9.0), EDTA and reduced glutathione were added to the resulting solution to make 4 L (final concentration: 1.0M of guanidine hydrochloride, 0.04M of glycine, 1mM of EDTA and 0.2 mM of reduced glutathione). The obtained solution was let stand at room temperature over night for refolding. The solution was concentrated by ultrafiltration (exclusion molecular weight: 6000). A crude product was obtained from the solution by salting out with 25% to 55% saturation of ammonium sulfate. The crude product was dissolved in 50 mM phosphate buffer (pH 7.5, and containing 0.5M of guanidine hydrochloride and 0.6M of ammonium sulfate), and insoluble matter was removed by centrifugation. The supernatant was absorbed in a phenyl Sepharose (Pharmacia Co.) column which was equilibrated with the same buffer, and sufficiently washed with the same buffer, then eluted with the same buffer but not containing ammonium sulfate to collect the elution fraction containing the intended product. This fraction was adsorbed on a Zn-chelate (Cu chelate for ACUK (−,q) and FCUK (−,q)) Sepharose (Pharmacia Co.) column, sufficiently washed with 50 mM phosphate buffer (pH 6.0, and containing 0.5M of NaCl), and eluted with 20 mM acetic acid buffer (pH 5.4, and containing 5M of NaCl). The elution fraction containing the intended product was concentrated and desalted using a ultrafiltration membrane PM-10 (Amicon Co.) (if necessary, it was passed through a benzamidine Sepharose column to remove the active form).

Thus a purified product corresponding to each of the human prourokinase-like polypeptides of this invention, AHUK (q,q), APUK (q,q), APUK (k,q), APUK (k,d), APUK (k,k), FPUK (q,q), ACUK (−,q), FCUK (−,q), V1PUK (k,q) and V2PUK (k,q), was obtained.

REFERENCE EXAMPLE 1

Preparation of plasmids pMUT90pml and p9420

A DNA fragment containing prelilac p/o, which was isolated after plasmid pPLL was digested with restriction enzymes Aat II and Xba I, and about 3.4 kb of DNA fragment containing laqI$^q$ gene, which was isolated after plasmid pMJR1560 (Amersham Co.) was digested with restriction enzyme Pst I, followed by treatment with T4DNA polymerase and digestion with restriction enzyme Aat II, and synthesized oligomer CroS/D-A/B were linked with T4DNA ligase to give plasmid p9410.

DNA fragment containing vector fragment, which was isolated after pMUT8L harboring natural human prourokinase gene was digested with restriction enzyme Nco I, was linked by T4DNA ligase to give plasmid p6514.

Plasmid p6514 was digested with restriction enzyme EcoR I and followed by treatment with Klenow fragment to fill in the restriction site, then linked by T4DNA ligase to give plasmid p6516.

About 4.2 kb of DNA fragment isolated after plasmid p6516 was digested with restriction enzyme BamH I was treated with Klenow fragment to fill in the restriction site, then linked by T4 DNA ligase to give plasmid p6610.

About 3.7 kb of DNA fragment isolated after plasmid pMUT9Lpml (with a human prourokinase derivatives gene of which lysine at the 135th position of the amino acid sequence of natural human prourokinase was substituted by glutamine), which was produced from plasmid pMUT8L, was digested with restriction enzymes Nar I and Nco I, and about 0.6 kb of DNA fragment isolated after plasmid p6610 was digested with restriction enzymes Nar I and Nco I were linked by T4 DNA ligase to give plasmid pMUT90pml.

A DNA fragment containing prelilac p/o, which was isolated after plasmid p9410 was digested with restriction enzyme Kpn I, treated with T4 DNA polymerase and further digested with restriction enzyme Aat II, and about 3.5 kb of DNA fragment containing tac p/o, which was isolated after plasmid pMUT90pml was digested with restriction enzyme Pst I, treated with T4 DNA polymerase and further digested with restriction enzyme Aat II were linked by T4 DNA ligase to give plasmid p9420.

REFERENCE EXAMPLE 2

Preparation of plasmids pHUK (q,d)/0 and pHUK (q,q)/0

About 4.4 kb of DNA fragment isolated after plasmid pMUT8L harboring human prourokinase gene was digested with restriction enzymes Axy I and Hind III was treated with Klenow fragment to fill in the restriction site, then linked by T4 DNA ligase to give plasmid pMUT4H.

About 3.1 kb of DNA fragment isolated after plasmid pMUT4H was digested with restriction enzymes Acc III and Nar I and about 1.3 kb of DNA fragment isolated after plasmid pMUT90pml was digested with restriction enzymes Acc III and Nar I were linked by T4 DNA ligase to give plasmid p6028.

About 3.7 kb of DNA fragment isolated after plasmid p6028 was digested with restriction enzymes Eco47 III and Hind III was treated with Klenow fragment to fill in the restriction site, then linked by T4 DNA ligase to give plasmid p6N17.

About 3.7 kb of DNA fragment isolated after plasmid p6N17 was digested with restriction enzymes Dra II and EcoR I, and each of synthesized oligomers TUK1-A/B and TUK2-A/B were linked by T4 DNA ligase to give plasmid p7214 and plasmid p7224, respectively.

About 3.8 kb of DNA fragment isolated after plasmid pMUT90pml was digested with restriction enzyme Ban II, and each of about 0.5 kb of DNA fragments isolated after plasmids p7214 and p7224 were each digested with restriction enzyme Ban II were linked by T4 DNA ligase to give plasmids pHUK (q,q)/0 and pHUK (q,d)/0, respectively.

REFERENCE EXAMPLE 3

Preparation of urokinase-like polypeptide ATUK (q,q) of which a peptide with ability to form bond with fibrin is added to the NH2 terminal side 100,000 units of purified sample of human prourokinase-like polypeptide AHUK (q,q) obtained in Example 5 was dissolved in 100 ul of 50 mM Tris hydrochloric acid buffer (pH 7.5) containing 0.1M NaCl, to which 0.015 cu of serum plasmin (Green Cross Co.) was added to incubate at 37° C. for an hour. Then 10 μg of trypsin inhibitor (Sigma Chemical Co.) was added to stop the reaction. The product was adsorbed in benzamidine Sepharose column, and eluted with 20 mM acetic acid buffer (pH 4.5) containing 0.5M NaCl. The eluted fractions were concentrated and desalted using ultrafiltration membrane PM-10 (AMICON Co.) to give urokinase-like polypeptide ATUK (q,q). Analysis of the amino acid sequence in the neighborhood of the NH2 terminal confirmed that the purified sample was urokinase-like polypeptide with the same sequence as that in the neighborhood of the NH2 terminal of prourokinase-like polypeptide AHUK (q,q).

It is believed that the human prourokinase-like polypeptides of this invention bind by covalent bonding with blood clots through the enzymatic action of the blood coagulation factor XIII (active form) which appears at the region where blood clots are formed, and then are converted to activated form which does not leave from the blood clot. Therefore the polypeptides of this invention can be an ideal thrombolytic agent which is very clot-specific, has less side effects such as systemic hemorrhage, and is not inhibited by plasminogen activator inhibitor I. The polypeptides of this invention can be economically manufactured by gene engineering methods.

TEST EXAMPLE 1

Fibrin binding ability test

The binding ability of each of purified human prourokinase-like polypeptides of this invention (hereinafter referred to as test sample) to a fibrin clot was compared with that of tPA, human prourokinase and urokinase-like polypeptide ATUK (q,q). The binding test was carried out according to the following two methods:

Reagents:
1) Tris-hydrochloric acid buffer; 50 mM of Tris, 38 mM of NaCl, 0.01% of Triton X-100, pH 7.5
2) Fibrinogen solution; 10 mg of plasminogen free human fibrinogen of Sigma Chemical Co./ml of Tris-hydrochloric acid buffer
3) Thrombin solution; 100 units of human thrombin of Sigma Chemical Co./ml of Tris-hydrochloric acid buffer
4) Plasmin solution; 15 cu of serum plasmin of Green Cross Co./ml of $H_2O$
5) Trypsin inhibitor solution; 5 mg of trypsin inhibitor of Sigma Chemical Co./ml of $H_2O$
6) Hirudin; Hirudin of Sigma Chemical Co.
7) Test sample solution; 5000 international units of test sample/ml of Tris-hydrochloric acid buffer I. Testing method of binding ability in fibrin clotting process Into a 1.5-ml eppendorf tube, while cooled with ice, were placed 75 μl of fibrinogen solution, 5 μl of 0.1M $CaCl_2$ aqueous solution and 100 μ of each test sample, to which the Tris-hydrochloric acid buffer was added to make 297 μl 1 and mixed well. 3 μl of thrombin solution was added to the solution to mix to treated for 60 minutes in a water bath of 37° C. Fibrin clots were thus formed. Immediately the clots were centrifuged at 4° C. (16,000 rpm, 10 minutes). The precipitate was washed with Tris-hydrochloric acid buffer. 1 NIH of hirudin and 5 to 15 μl of plasmin solution were added to dissolve the precipitate and simultaneously the test sample was activated. A trypsin inhibitor of volume of 5 fold-weight of plasmin was added to inhibit the plasmin activity. An amount of test sample was measured from the degradation activity of synthesized substrate S-2444 of Kabi Co., being the amount of test sample bound.

II. Testing method of binding ability after fibrin clots are formed

Method I was repeated except that fibrin clots were formed with no addition of test sample, then 100 μl of test sample solution and 200 μl of Tris-hydrochloric acid buffer were added and maintained for 60 minutes in a water bath of 37° C. An amount of test sample in the centrifuged precipitate obtained by the same treatment as that in I was measured.

In the above testing method, if the test samples were human prourokinase and APUK (k,k), the test was carried out in the presence of hirudin in order to prevent the test sample from losing activity by degradation by thrombin.

The binding ability of each of test samples to fibrin clots are shown in the following table:

$$\text{binding ratio} = \frac{\text{Amount of test sample bound}}{\text{Amount of test sample used}} \times 100$$

| test samples | binding ratio (%) in fibrin clotting process | binding ratio (%) after fibrin clotting were formed |
| --- | --- | --- |
| tPA | 66 | 51 |
| human urokinase* | 6 | 4 |
| HUK* | 10 | 7 |
| HUK (q,q) | 7 | 6 |
| ATUK (q,q) | 11 | 7 |
| AHUK (q,q) | 59 | 48 |
| APUK (q,q) | 58 | 45 |
| APUK (k,q) | 43 | 32 |
| APUK (k,d) | 64 | 55 |
| APUK (k,k) | 52 | 45 |
| ACUK (—,q) | 31 | 22 |
| FPUK (q,q) | 62 | 28 |
| FCUK (—,q) | 35 | 21 |
| $V_1$ PUK (k,q) | 52 | 30 |
| $V_2$ PUK (k,q) | 48 | 32 |

*human urokinase: urokinase extracted from human urine
*HUK: human prourokinase

The tPA and APUK (q,q), which were bound in the fibrin clotting process, left from the fibrin clots after bound were estimated at an hourly interval. It was recognized that tPA was left 23% after 2 hours and gradually was being left after it. To contrast, 8% of APUK (q,q) was left after 2 hours and no leaving was recognized after it.

TEST EXAMPLE 2

Fibrin lysis activity test

The lysis activity of each purified human prourokinase-like polypeptides of this invention (hereinafter referred to as test sample) to fibrin was measured using the standard urokinase (distributed by the National Institute of Hygiene Science) as a reference.

Testing method

Into 5 ml of 0.1M phosphate buffer (pH 7.4) containing 2% of bovine fibrinogen (Seikagaku Kogyo Co.) and 10 mM of $CaCl_2$ were added 5 ml of 0.25% aqueous solution of agarose which was heated to dissolve and 0.1 ml of bovine thrombin (Mochida Pharmaceutical Co.) solution (100 active units/ml). After mixing, the mixture was poured in a Petri dish of 9.0 cm in diameter to make a fibrin plate. On the fibrin plate was spotted each of 5 μl of test samples, each of which contained one unit of hirudin, and incubated at 37° C. for 18 hours. An activity value was calculated from the lysis circle. The lysis activity of each test sample per unit absorbance at 280 nm is shown in the following table in international unit.

| Test sample name | Fibrin lysis activity International unit/O.D.280 |
| --- | --- |
| AHUK (q,q) | $8.8 \times 10^4$ |
| APUK (q,q) | $10.9 \times 10^4$ |
| APUK (k,q) | $10.4 \times 10^4$ |
| APUK (k,d) | $8.7 \times 10^4$ |
| APUK (k,k) | $9.2 \times 10^4$ |
| FPUK (q,q) | $10.9 \times 10^4$ |
| ACUK (—,q) | $15.7 \times 10^4$ |
| FCUK (—,q) | $16.8 \times 10^4$ |
| $V_1P$ (k,q) | $9.7 \times 10^4$ |
| $V_2P$ (k,q) | $10.4 \times 10^4$ |

Figure 2:
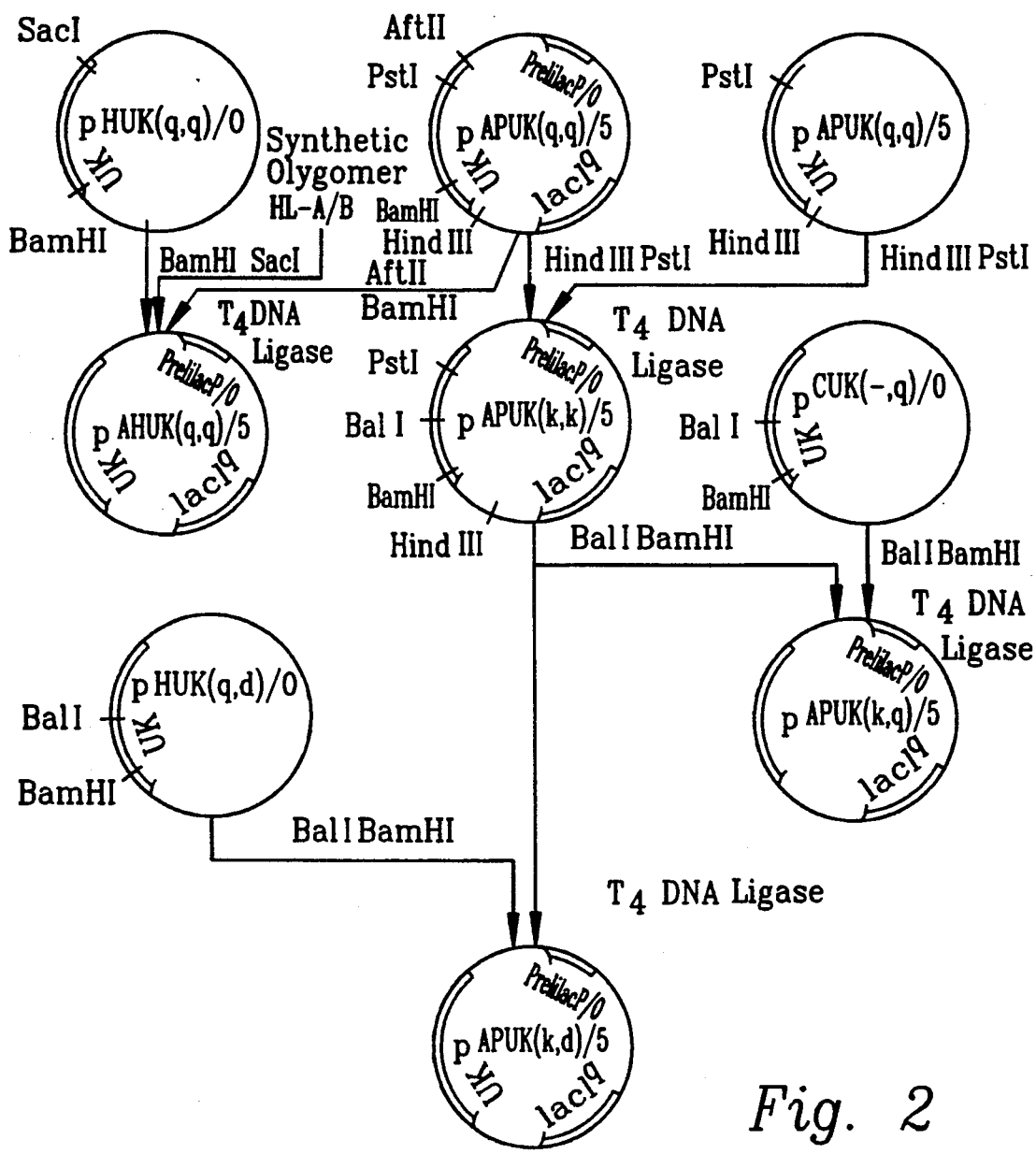
FIG. 2 is a schematic diagram for the preparation of plasmid as in Example 3.
Figure 3:
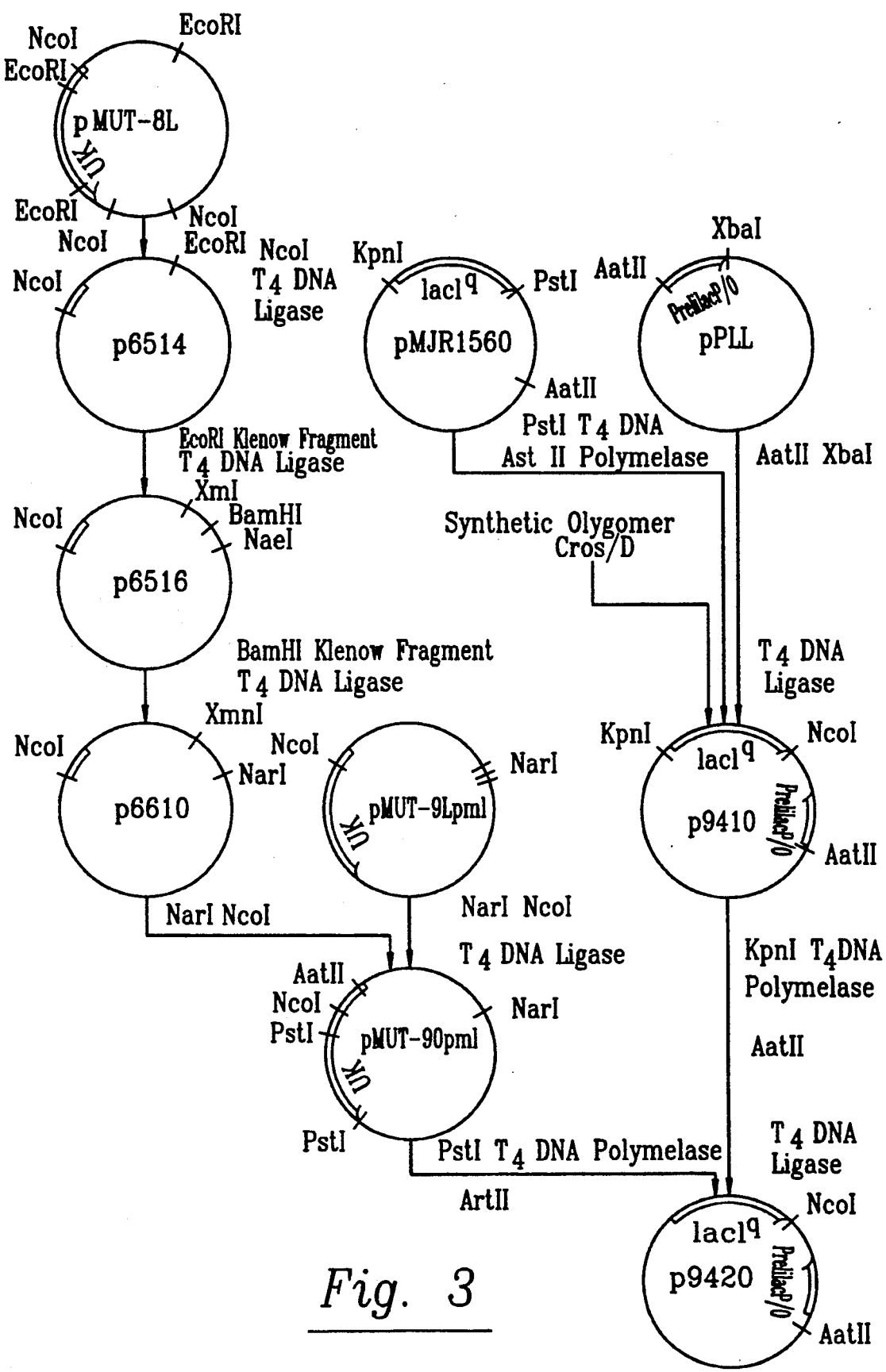
FIG. 3 is a schematic diagram for the preparation of plasmid as in Reference Example 1.
Figure 4:
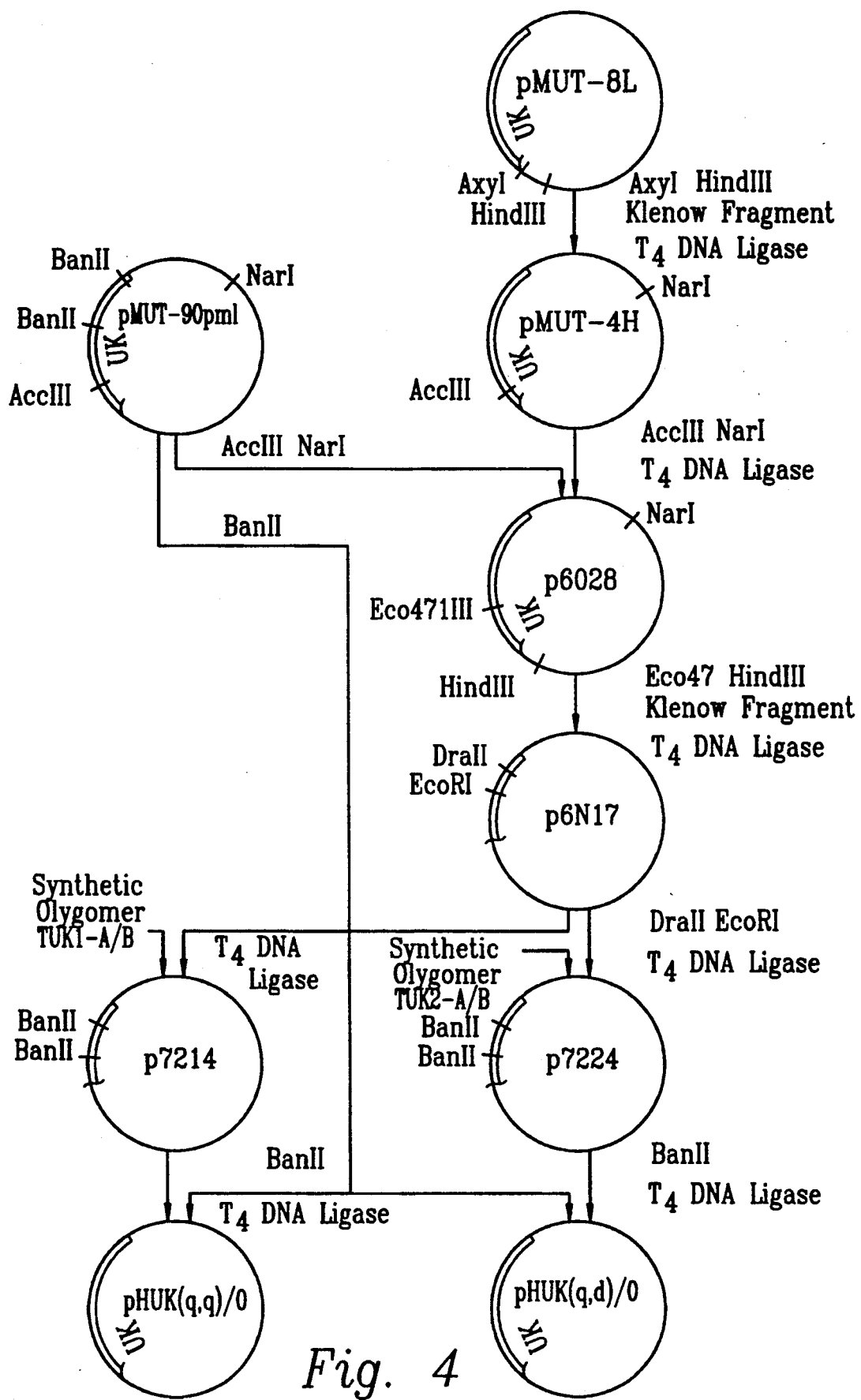
FIG. 4 is a schematic diagram for the preparation of plasmid as in Reference Example 2.

FIGS. 5-1 and 5-2 collectively depict the nucleotide sequence encoding the human prourokinase-like polypeptide FCUK (—,q), and the corresponding amino acid sequence using single letter abbreviations.

FIGS. 6-1, 6-2 and 6-3 collectively depict the nucleotide sequence encoding the human prourokinase-like polypeptide AHUK (q,q), and the corresponding amino acid sequence using single letter abbreviations.

FIGS. 7-1, 7-2 and 7-3 collectively depict the nucleotide sequence encoding the human prourokinase-like polypeptide APUK (k,k), and the corresponding amino acid sequence using single letter abbreviations.

FIGS. 8-1, 8-2 and 8-3 collectively depict the nucleotide sequence encoding the human prourokinase-like polypeptide APUK (k,q), and the corresponding amino acid sequence using single letter abbreviations.

Furthermore, the living organism described herein have been deposited at the Fermentation & Research Institute, 1-3, Higashi 1-Chome, Tsukaba-shi, Ibaraki-ken, 305, Japan.

Now that the invention has been described,

We claim:

1. A substantially pure, enzymatically-active, human prourokinase mutein comprising a human prourokinase derivative fused with an amino-terminal oligopeptide, said amino-terminal oligopeptide capable of forming a covalent bond with fibrin present in a blood clot through the enzymatic action of human blood coagulation factor XIII, wherein said prourokinase derivative is derived from the amino acid sequence $Ser^1$-$Leu^{411}$ of human prourokinase and consists essentially of an amino acid sequence selected from the group consisting of $Leu^4$-$Leu^{411}$, $Leu^4$-$Leu^{411}$ in which $lysine^{135}$ is substituted with a glutamine residue, $Leu^4$-$Leu^{411}$ in which $lysine^{135}$ and $arginine^{156}$ are both substituted with glutamine residues, $Leu^4$-$Leu^{411}$ in which $lysine^{135}$ is substituted with an aspartate residue and $arginine^{156}$ is substituted with a glutamine residue, $Leu^{144}$-$Leu^{411}$, and $Leu^{144}$-$Leu^{411}$ in which $arginine^{156}$ is substituted with a glutamine residue; and, wherein said amino terminal oligopeptide is selected from the group consisting of (Met.)Asn.Gln.Glu.Gln.Val.Ser.Pro.Leu.Thr.Leu.-Leu.Lys, (Met.)Gln.Ala.Gln.Gln.Met.Val.Gln.Pro.Gln.Ser.-Pro.Val.Ala.Val.Lys, (Met.)Ala.Gln.Lys.Met.Val.Gln.Pro.Leu.Thr.Leu.-Leu.Lys, (Met.)Ala.Gln.Lys.Met.Val.Gln.Pro.Gln.Thr.Leu.-Leu.Lys, (Met.)Gln.Glu.Gln.Val.Ser.Pro.Gln.Thr.Leu.Leu.Lys, (Met.)Asn.Gln.Asp.Gln.Val.Ser.Pro.Gln.Thr.Leu.Leu.Lys, (Met.)Asn.Gln.Glu.Asn.Val.Ser.Pro.Gln.Thr.Leu.Leu.Lys, and, (Met.)Asn.Gln.Ser.Met.Val.Ser.Pro.Gln.Thr.Leu.Leu.Lys.

2. An isolated and purified DNA segment consisting essentially of a region encoding a human prourokinase mutein of claim 1 an allelic variant or exhibiting equivalent biological activity, capable of hybridizing therewith under conditions allowing detection of 70%.

3. DNA segment of claim 2 further comprising a transcriptional promoter element in operable linkage with said region encoding a human prourokinase mutein, said promoter element useful as a promoter of gene expression in *E. coli*.

4. A DNA construct comprising a DNA sequence of claim 2 and a replication system capable of replication in an *E. coli* host cell.

5. A recombinant plasmid comprising a DNA sequence of claim 2 wherein said plasmid is a cloning vehicle and is capable of expressing a DNA sequence of claim 2 in a transformed *E. coli* host cell.

6. *E. coli* transformed with the plasmid according to claim 5.

7. The *E. coli* transformants of the DNA construct of claim 4 selected from the *E. coli* strain transformants consisting essentially of FERM BP-2467, FERM BP-2465, and FERM BP-2466.

* * * * *